(12) United States Patent
Hanson et al.

(10) Patent No.: US 10,695,487 B2
(45) Date of Patent: Jun. 30, 2020

(54) CONTROLLED DELIVERY DRIVE MECHANISMS FOR DRUG DELIVERY PUMPS

(71) Applicant: UNL Holdings LLC, New York, NY (US)

(72) Inventors: Ian B. Hanson, Wayne, PA (US); Paul F. Bente, IV, Wayne, PA (US); Mark A. Destefano, Collegeville, PA (US)

(73) Assignee: UNL Holdings LLC, New York, NY (US)

( * ) Notice: Subject to any disclaimer, the term of this patent is extended or adjusted under 35 U.S.C. 154(b) by 281 days.

(21) Appl. No.: 15/691,097

(22) Filed: Aug. 30, 2017

(65) Prior Publication Data

US 2018/0055995 A1      Mar. 1, 2018

Related U.S. Application Data

(60) Provisional application No. 62/381,377, filed on Aug. 30, 2016.

(51) Int. Cl.
    *A61M 5/168*      (2006.01)
    *A61M 5/142*      (2006.01)
    (Continued)

(52) U.S. Cl.
    CPC .......... *A61M 5/168* (2013.01); *A61M 5/1454* (2013.01); *A61M 5/14216* (2013.01);
    (Continued)

(58) Field of Classification Search
    CPC ............ A61M 5/14216; A61M 5/1454; A61M 5/172; A61M 5/141; A61M 5/14566;
    (Continued)

(56) References Cited

U.S. PATENT DOCUMENTS 3,631,847 A    1/1972   Hobbs, II
3,701,345 A    10/1972   Heilman
(Continued)

FOREIGN PATENT DOCUMENTS

EP    1 702 635 A2    9/2006
EP    1 341 569 B1    1/2007
(Continued)

OTHER PUBLICATIONS

International Search Report and Written Opinion dated Nov. 29, 2017 for International Application No. PCT/IB2017/001047, entitled "Controlled Delivery Drive Mechanisms for Drug Delivery Pumps."
(Continued)

*Primary Examiner* — Lauren P Farrar
*Assistant Examiner* — James D Ponton
(74) *Attorney, Agent, or Firm* — Hamilton, Brook, Smith & Reynolds, P.C.

(57) ABSTRACT

A controlled delivery drive mechanism includes a drive housing, a piston, and a biasing member initially retained in an energized state and is configured to bear upon an interface surface of the piston. The piston is configured to translate a plunger seal and a barrel. A tether is connected between the piston and the winch drum to restrain the free expansion of the biasing member and the free axial translation of the piston upon which the biasing member bears upon. The drive mechanism may further include a gear assembly and an escapement regulating mechanism configured to control the rotation of the gear assembly to release the tether from the winch drum. The metering of the tether by the escapement regulating mechanism controls the rate or profile of drug delivery to a user.

20 Claims, 9 Drawing Sheets

(51) Int. Cl.
    *A61M 5/145*     (2006.01)
    *A61M 5/172*     (2006.01)
    *A61M 5/14*     (2006.01)

(52) U.S. Cl.
    CPC ............. *A61M 5/172* (2013.01); *A61M 5/141* (2013.01); *A61M 5/14566* (2013.01); *A61M 2005/1426* (2013.01); *A61M 2005/14208* (2013.01); *A61M 2005/14252* (2013.01); *A61M 2205/13* (2013.01); *A61M 2205/18* (2013.01); *A61M 2205/3334* (2013.01); *A61M 2205/3365* (2013.01); *A61M 2207/00* (2013.01)

(58) Field of Classification Search
    CPC ......... A61M 2005/14208; A61M 2005/14252; A61M 5/168; A61M 5/16804; A61M 5/16877; F04B 13/00; F04B 19/04; F04B 19/22; F04B 35/01; F04B 35/144
    See application file for complete search history.

(56) References Cited

U.S. PATENT DOCUMENTS

| | | |
|---|---|---|
| 4,004,586 A | 1/1977 | Christensen et al. |
| 4,313,439 A | 2/1982 | Babb |
| 4,565,543 A | 1/1986 | Bekkering et al. |
| 4,602,700 A | 7/1986 | Szabo |
| 4,673,400 A | 6/1987 | Martin |
| 4,676,122 A | 6/1987 | Szabo et al. |
| 4,685,903 A | 8/1987 | Cable et al. |
| 4,755,173 A | 7/1988 | Konopka et al. |
| 4,840,620 A | 6/1989 | Kobayashi et al. |
| 4,921,487 A | 5/1990 | Buffet et al. |
| 5,167,816 A | 12/1992 | Kruger et al. |
| 5,747,350 A | 5/1998 | Sattler |
| 5,795,339 A | 8/1998 | Erskine |
| 5,858,001 A | 1/1999 | Tsais et al. |
| 5,919,167 A | 7/1999 | Mulhauser et al. |
| 6,248,093 B1 | 6/2001 | Moberg |
| 6,645,177 B1 | 11/2003 | Shearn |
| 6,699,218 B2 | 3/2004 | Flaherty et al. |
| 7,063,684 B2 | 6/2006 | Moberg |
| D564,087 S | 3/2008 | Yodfat et al. |
| D585,543 S | 1/2009 | Yodfat et al. |
| 7,479,135 B2 | 1/2009 | Richter et al. |
| 7,611,503 B2 | 11/2009 | Spohn et al. |
| 7,780,636 B2 | 8/2010 | Radmer et al. |
| 7,803,134 B2 | 9/2010 | Sharifi et al. |
| 7,846,132 B2 | 12/2010 | Gravesen et al. |
| 7,879,010 B2 | 2/2011 | Hunn et al. |
| 7,905,859 B2 | 3/2011 | Bynum et al. |
| 7,927,306 B2 | 4/2011 | Cross et al. |
| 7,967,795 B1 | 6/2011 | Cabiri |
| 8,029,472 B2 | 10/2011 | Leinsing et al. |
| 8,048,031 B2 | 11/2011 | Shaw et al. |
| 8,152,771 B2 | 4/2012 | Mogensen et al. |
| 8,157,769 B2 | 4/2012 | Cabiri |
| 8,162,892 B2 | 4/2012 | Mogensen et al. |
| 8,167,844 B2 | 5/2012 | Dillard, III |
| 8,187,232 B2 | 5/2012 | Chong et al. |
| D669,165 S | 10/2012 | Estes et al. |
| 8,795,234 B2 | 8/2014 | Kadamus et al. |
| 8,939,935 B2 | 1/2015 | O'Connor et al. |
| 9,005,169 B2 | 4/2015 | Gravesen et al. |
| 9,987,419 B2 | 6/2018 | Hanson et al. |
| 10,092,693 B2 | 10/2018 | Hanson et al. |
| 2002/0123740 A1 | 9/2002 | Flaherty et al. |
| 2004/0039344 A1 | 2/2004 | Baldwin et al. |
| 2004/0092878 A1 | 5/2004 | Flaherty |
| 2005/0171476 A1 | 8/2005 | Judson |
| 2005/0197625 A1* | 9/2005 | Haueter ............... A61M 5/1454 604/131 |
| 2007/0010789 A1 | 1/2007 | Peter et al. |
| 2007/0059989 A1 | 3/2007 | Kura et al. |
| 2007/0073228 A1 | 3/2007 | Mernoe et al. |
| 2007/0179444 A1 | 8/2007 | Causey et al. |
| 2008/0132842 A1 | 6/2008 | Flaherty |
| 2008/0269687 A1 | 10/2008 | Chong et al. |
| 2009/0093792 A1 | 4/2009 | Gross et al. |
| 2009/0124979 A1 | 5/2009 | Raymond et al. |
| 2009/0145509 A1 | 6/2009 | Baker et al. |
| 2009/0204077 A1 | 8/2009 | Hasted et al. |
| 2009/0240240 A1 | 9/2009 | Hines et al. |
| 2011/0098652 A1 | 4/2011 | Hasted et al. |
| 2011/0166509 A1 | 7/2011 | Gross et al. |
| 2011/0301534 A1 | 12/2011 | Renz et al. |
| 2012/0035546 A1 | 2/2012 | Cabiri |
| 2012/0123354 A1 | 5/2012 | Woehr |
| 2012/0172804 A1* | 7/2012 | Plumptre .......... A61M 5/14244 604/154 |
| 2013/0060196 A1 | 3/2013 | O'Connor et al. |
| 2013/0060233 A1* | 3/2013 | O'Connor ............. A61M 5/158 604/506 |
| 2014/0200510 A1 | 7/2014 | Agard et al. |
| 2015/0119797 A1 | 4/2015 | Cabin |
| 2015/0141920 A1 | 5/2015 | O'Connor et al. |
| 2015/0209505 A1* | 7/2015 | Hanson ............... A61M 5/1454 604/135 |
| 2015/0217045 A1 | 8/2015 | Bente, IV et al. |
| 2015/0297827 A1 | 10/2015 | Hanson et al. |
| 2018/0243502 A1 | 8/2018 | Hanson et al. |

FOREIGN PATENT DOCUMENTS

| | | |
|---|---|---|
| EP | 1 427 471 B1 | 2/2008 |
| EP | 1 695 727 B1 | 7/2008 |
| EP | 1 513 580 B1 | 3/2009 |
| EP | 2 077 128 A1 | 7/2009 |
| EP | 2 379 134 A1 | 10/2011 |
| EP | 2 429 612 A1 | 3/2012 |
| EP | 2 433 663 A1 | 3/2012 |
| EP | 2 890 433 A2 | 7/2015 |
| EP | 3 028 727 B1 | 6/2016 |
| GB | 2166497 A | 5/1986 |
| GB | 2 452 286 A | 3/2009 |
| JP | S62-217975 A | 9/1987 |
| JP | 2002-503122 A | 1/2002 |
| JP | 2004-195227 A | 7/2004 |
| JP | 2005-537112 A | 12/2005 |
| JP | 2009-101217 A | 5/2009 |
| JP | 2010-527255 A | 8/2010 |
| JP | 2010-538799 A | 12/2010 |
| JP | 2010-540156 A | 12/2010 |
| JP | 2011-523873 A | 8/2011 |
| WO | WO 98/56439 A1 | 12/1998 |
| WO | WO 1999/020327 A2 | 4/1999 |
| WO | WO 1999/048546 A1 | 9/1999 |
| WO | WO 2002/028455 | 4/2002 |
| WO | WO 2003/024504 A2 | 3/2003 |
| WO | WO 2003/103763 A1 | 12/2003 |
| WO | WO 2004/062714 A1 | 7/2004 |
| WO | WO 2005/037350 A2 | 4/2005 |
| WO | WO 2007/128767 A1 | 11/2007 |
| WO | WO 2008/024808 A2 | 2/2008 |
| WO | WO 2008/142394 A1 | 11/2008 |
| WO | WO 2009/039214 A1 | 3/2009 |
| WO | WO 2009/125582 A1 | 10/2009 |
| WO | WO 2009/149547 A1 | 12/2009 |
| WO | WO 2010/029054 A1 | 3/2010 |
| WO | WO 2010/077807 A1 | 7/2010 |
| WO | WO 2010/084113 A1 | 7/2010 |
| WO | WO 2010/085338 A1 | 7/2010 |
| WO | 2010/112376 A1 | 10/2010 |
| WO | 2010/112377 A1 | 10/2010 |
| WO | WO 2010/132196 A1 | 11/2010 |
| WO | WO 2011/006652 A1 | 1/2011 |
| WO | WO 2011/046950 A1 | 4/2011 |
| WO | WO 2011/090956 A2 | 7/2011 |
| WO | WO 2011/121023 A1 | 10/2011 |
| WO | WO 2011/133823 A1 | 10/2011 |
| WO | WO 2012/032411 A2 | 3/2012 |
| WO | WO 2012/085029 A1 | 6/2012 |

(56) References Cited

FOREIGN PATENT DOCUMENTS

| WO | WO 2012/131044 A1 | 10/2012 |
|----|---|---|
| WO | 2013/033421 A2 | 3/2013 |
| WO | 2013/040032 A1 | 3/2013 |
| WO | WO 2013/033467 A2 | 3/2013 |
| WO | WO 2013/040032 A1 | 3/2013 |
| WO | 2013/153041 A2 | 10/2013 |
| WO | WO 2013/156224 A1 | 10/2013 |
| WO | 2014/036239 A2 | 3/2014 |
| WO | 2014/036308 A2 | 3/2014 |
| WO | 2014/116274 A1 | 7/2014 |
| WO | 2016/049501 A1 | 3/2016 |
| WO | 2017/177094 A2 | 10/2017 |
| WO | WO 2019/043423 A1 | 3/2019 |

OTHER PUBLICATIONS

International Preliminary Report on Patentability dated Mar. 3, 2015 for International Application No. PCT/US2013/057367, entitled "Controlled Delivery Drive Mechanisms for Drug Delivery Pumps".
International Search Report and Written Opinion dated May 27, 2014 for International Application No. PCT/US2013/057367 entitled "Controlled Delivery Drive Mechanisms for Drug Delivery Pumps".

\* cited by examiner

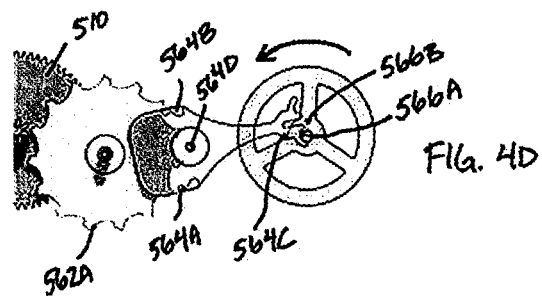
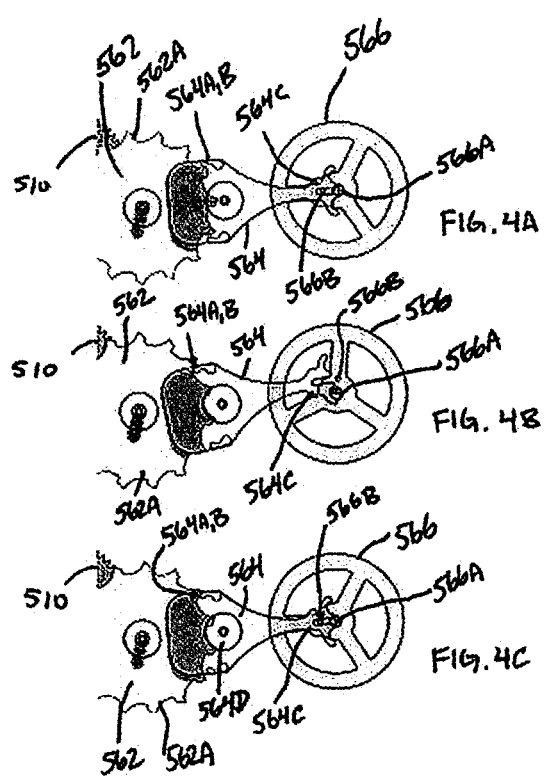

CONTROLLED DELIVERY DRIVE MECHANISMS FOR DRUG DELIVERY PUMPS

RELATED APPLICATION

This application claims the benefit of U.S. Provisional Application No. 62/381,377, filed on Aug. 30, 2016. The entire teachings of this application are incorporated herein by reference.

FIELD

This invention relates to drug delivery pumps. More particularly, this invention relates to drive mechanisms for the controlled delivery of drug substances, drug delivery pumps with controlled delivery drive mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

Drive mechanisms for the controlled delivery of drug substances are provided, as well as drug delivery pumps with controlled delivery drive mechanisms, methods of operating such devices, and methods of assembling such devices. Notably, the drive mechanisms of the present invention control a rate of drug delivery by metering, providing resistance, or otherwise preventing free axial translation of a plunger seal utilized to force a drug substance out of a drug container. Such drive mechanisms also provide for a smaller footprint, enabling their use in more compact drug delivery pumps, while also being capable of delivering drug substances at variable rates. The controlled delivery drive mechanisms of the present invention may be pre-configurable or dynamically configurable, such as by control by the power and control system, to meet desired delivery rates or profiles, as explained in detail below. Additionally, drive mechanisms of the present invention can provide integrated status indication features to provide feedback to a user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. Because the end-of-dose indication is related to the physical end of axial translation of one or more components of the drive mechanism, the drive mechanism and drug pump provide a true end-of-dose indication to the user. Through these mechanisms, confirmation of drug dose delivery can accurately be provided to the user or administrator. Accordingly, the novel devices of the present invention alleviate one or more of the problems associated with prior art devices, such as those referred to above.

In a first embodiment, the present invention provides a controlled delivery drive mechanism which includes a drive housing, a piston, and one or more biasing members, wherein the one or more biasing members are initially retained in an energized state and is configured to bear upon an interface surface of the piston. The piston is configured to translate substantially axially within a drug container having a plunger seal and a barrel. A tether is connected at one end to the piston and at another end to a winch drum of a regulating mechanism. The tether restrains the free expansion of the biasing member from its initial energized state, thereby also restraining the free axial translation of the piston upon which the biasing member bears upon. The tether is configured to be released from a winch drum of the regulating mechanism, providing controlled expansion of the biasing member.

The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism.

In at least one embodiment, the regulating mechanism is an escapement regulating mechanism coupled to, or acting with, the winch drum. The escapement regulating mechanism may further include a gear train having one or more gears, wherein the rotation of at least one gear of the gear train is coupled to the rotation of the winch drum. In a particular embodiment, the escapement regulating mechanism further includes a lever and an escape wheel configured to engage and meter the rotational movement of the gear train. The lever has pins and a prong, wherein the prong movably engages a post and is configured to removably engage an impulse pin of a balance wheel, and wherein the balance wheel engages and is capable of oscillating around a post in combination with a hair spring. An electromechanical actuator such as a motor or solenoid may additionally be used to control the oscillation and/or rotation of the balance wheel. For example, a DC or stepper motor may be used, or a linear or rotary solenoid may be used. The escape wheel is a compound gear having escape teeth around the circumference of a large diameter escape gear and a small diameter gear configured to engage and meter the gear train. The metering of the gear train and/or winch drum by an escapement regulating mechanism controls the rate or profile of drug delivery to a user.

The gear train may include a winch gear coupled to a winch drum upon which the tether may be releasably wound. The winch gear may be configured to engage a first compound gear, such that rotation of the winch gear and the small gear of the first compound gear are linked. The gear assembly may additionally include a second compound gear, wherein the large gear of the first compound gear is engaged with the small gear of the second compound gear. The large gear of the second compound gear may be engaged with a gear of the escape wheel such that rotation of the second compound gear and escape wheel are coupled. In this way rotation of the escape wheel is coupled to rotation of the winch drum and can thereby control the release of the tether from the winch drum to meter the free expansion of the biasing member from its initial energized state and the free axial translation of the piston upon which the biasing member bears upon. The metering of the tether by the regulating mechanism controls the rate or profile of drug delivery to a user. The piston may be one or more parts and connects to a distal end of the tether.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present invention provides a drug delivery pump with controlled drug delivery. The drug delivery pump includes a housing and/or an assembly platform, upon which an activation mechanism, an insertion mechanism, a fluid pathway connection, a power and control system, and a controlled delivery drive mechanism may be mounted. The drive mechanism includes a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum of the delivery regulating mechanism to meter the free expansion of the biasing member from its initial energized state and the free axial translation of the piston upon which the biasing member bears upon.

In another embodiment, the drug pump further includes a gear assembly. The gear assembly may include a winch gear connected to a winch drum upon which the tether may be releasably wound, rotation of the winch drum releases the tether from the winch drum to meter the free expansion of the biasing member from its initial energized state and the free axial translation of the piston upon which the biasing member bears upon. The metering of the tether controls the rate or profile of drug delivery to a user. The piston may be one or more parts and connects to a distal end of the tether. The winch drum is coupled to a regulating mechanism which controls rotation of the winch drum and hence metering of the translation of the piston.

The drug pump may utilize the regulating mechanism described above in the first embodiment, which configuration utilizes an escapement regulating mechanism to control the metering of the tether. The escapement regulating mechanism may further include a gear train having one or more gears. In a particular embodiment, the escapement regulating mechanism further includes a lever and an escape wheel configured to engage and meter the rotational movement of the gear train. The lever has pins and a prong, wherein the prong movably engages a post and is configured to removably engage an impulse pin of a balance wheel, and wherein the balance wheel engages and is capable of oscillating around a post in combination with a hair spring. A motor, such as a DC motor or stepper motor, or a linear or rotary solenoid may additionally be used to control the oscillation and/or rotation of the balance wheel. The escape wheel is a compound gear having escape teeth around the circumference of a large diameter escape gear and a small diameter gear configured to engage and meter the gear train. The metering of the gear train by an escapement regulating mechanism controls the rate or profile of drug delivery to a user. The piston is configured to contact and axially translate the plunger seal within the barrel.

In yet another embodiment, the drug pump may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug pump is configured to receive one or more inputs to meter the release of the tether by the winch drum and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch drum on the free axial translation of the piston upon which the biasing member bears upon to meet a desired drug delivery rate or profile, to change the dose volume for delivery to the user, and/or to otherwise start, stop, or pause operation of the drive mechanism.

A method of assembling a drug delivery pump includes attaching a controlled delivery drive mechanism, an insertion mechanism, a fluid pathway connection, and a power and control system to an assembly platform and/or a housing of the drug pump.

A method of operating a drug delivery pump includes restraining expansion of at least one biasing member with a tether and metering release of the tether with an escapement regulating mechanism. The tether is connected at one end to a piston having an interface surface and at another end to a winch drum. The biasing member, initially retained in an energized state, is configured to bear upon the interface surface of the piston, and, upon metered release of the tether by the winch drum, the biasing member is configured to cause release of a drug from the pump.

The novel embodiments of the present invention provide for drive mechanisms that are capable of metering, providing resistance, or otherwise preventing free axial translation of a plunger seal utilized to force a drug substance out of a drug container and, thereby, control a rate of delivery of drug substances. Embodiments of the present invention, in which a tether is provided to restrain expansion of a biasing member, also provide for a more compact design than drive mechanisms requiring a lengthier piston. In addition, as force to translate a plunger seal is provided by the biasing member, with the biasing member being restrained by tether that is metered by an escapement regulating mechanism, power and control systems are optional in drug delivery pumps of the present invention, providing for an even further space-saving design.

The novel control delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. For example, the embodiments may include one or more batteries utilized to power the motor, drive mechanisms, and drug pumps of the present invention. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIGS. 4A-4C shows an enlarged view of an escapement regulating mechanism of a drive mechanism, according to at least one embodiment of the present invention;

FIGS. 4D-4H shows the progression of the escapement regulating mechanism, according to the embodiment shown in FIGS. 4A-4C, during operation;

DETAILED DESCRIPTION

Figure 1A:
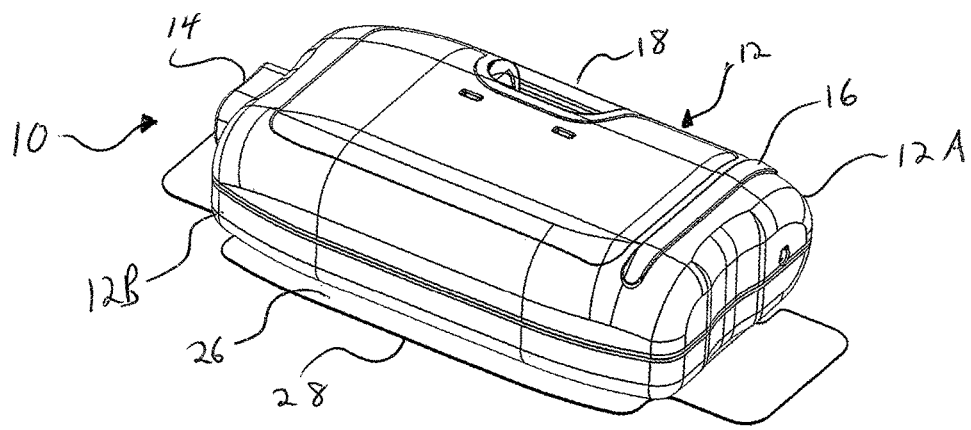
FIG. 1A shows an isometric view of a drug delivery pump having a controlled delivery drive mechanism, according to one embodiment of the present invention.

The present invention provides drive mechanisms for the controlled delivery of drug substances and drug delivery pumps that incorporate such controlled delivery drive mechanisms. The drive mechanisms of the present invention control the rate of drug delivery by metering, providing resistance, or otherwise preventing free axial translation of the plunger seal utilized to force a drug substance out of a drug container and, thus, are capable of delivering drug substances at variable rates and/or delivery profiles. The drive mechanisms include a tether configured to restrain expansion of a biasing member, thereby providing for a more compact design than drive mechanisms requiring a lengthier piston. Additionally, the drive mechanisms of the present invention can provide for integrated status indication features, such as with status triggers located on a tether of the device, which can provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the drug pumps. According to various aspects and embodiments described herein, reference is made to a "biasing member", such as in the context of one or more biasing members for asserting force on a plunger seal. It will be appreciated that the biasing member may be any member that is capable of storing and releasing energy. Non-limiting examples include a spring, such as for example a coiled spring, a compression or extension spring, a torsional spring, or a leaf spring, a resiliently compressible or elastic band, or any other member with similar functions. In at least one embodiment of the present invention, the biasing member is a spring, preferably a compression spring.

The novel devices of the present invention provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pumps, drive mechanisms, and their respective components are described further herein with reference to the accompanying figures.

Figure 1B:
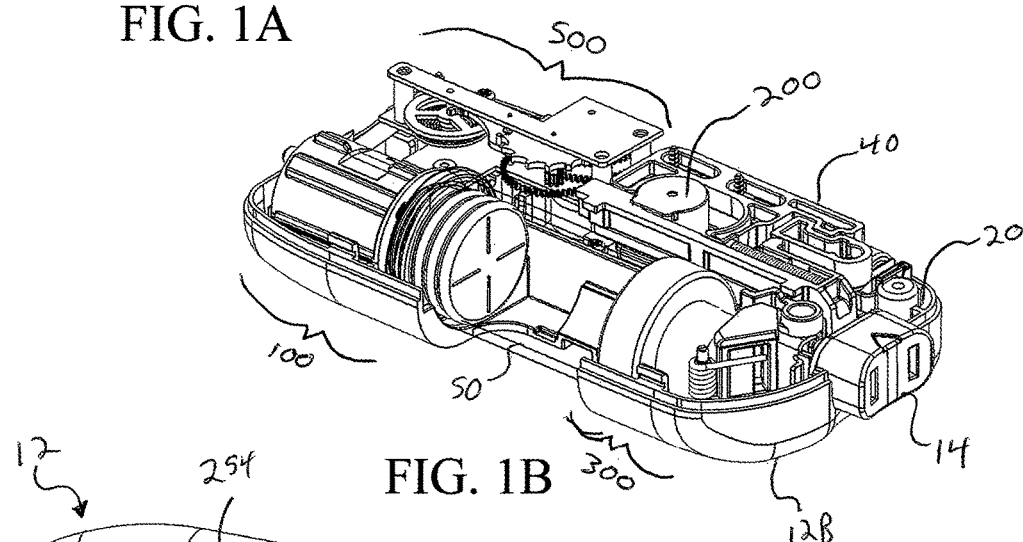
FIG. 1B shows an isometric view of the interior components of the drug delivery pump shown in FIG. 1A (shown without the adhesive patch)
Figure 1C:
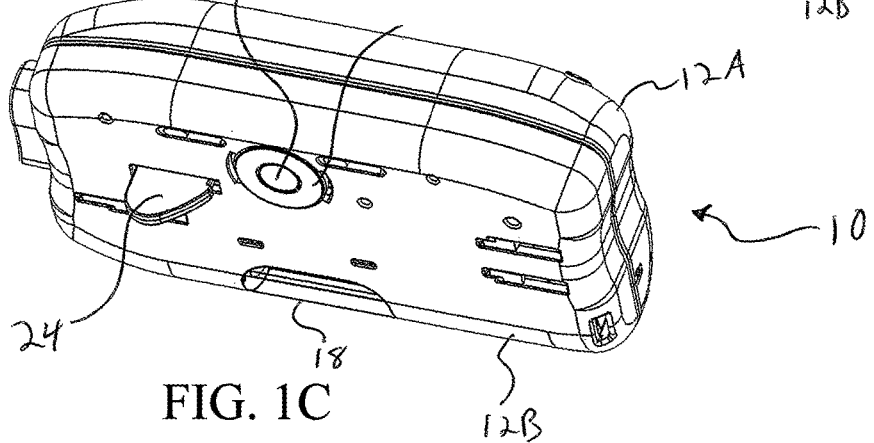
FIG. 1C shows an isometric view of the bottom of the drug delivery pump shown in FIG. 1A (shown without the adhesive patch)
Figure 7:
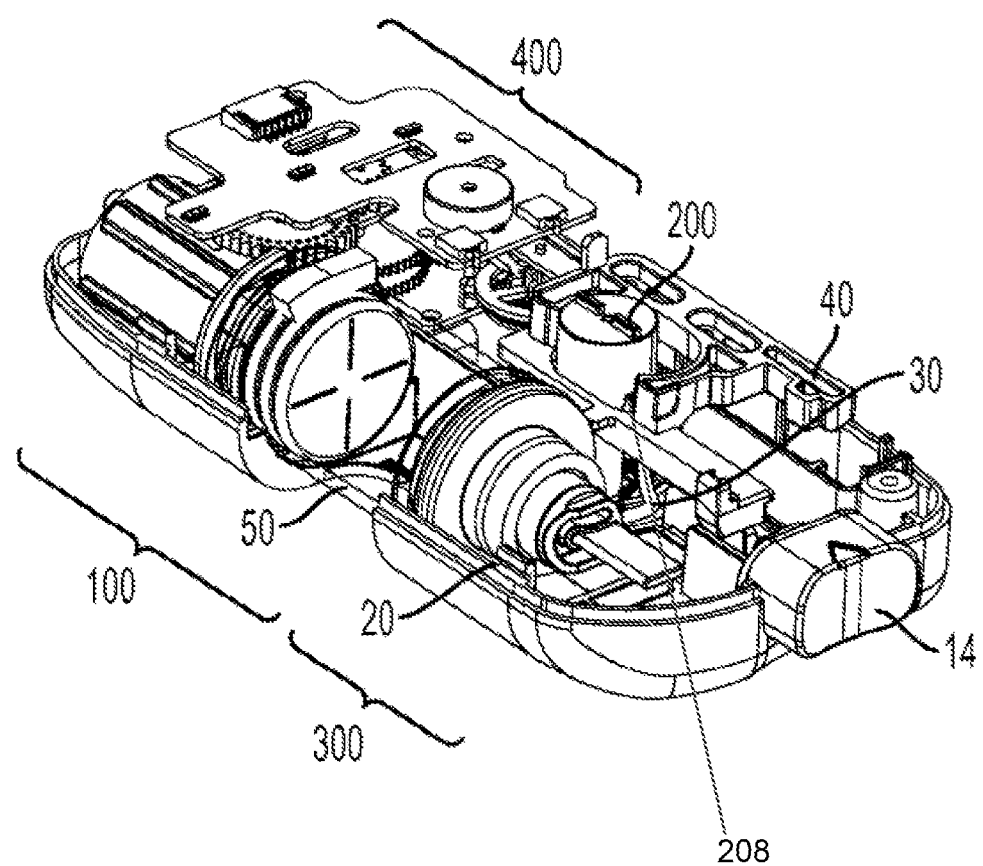
FIG. 7 shows an isometric view of another configuration of interior components of a drug delivery pump.

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing sub-components which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump 10 further includes assembly platform 20, drive mechanism 100 having drug container 50, insertion mechanism 200, and a fluid pathway connection 300. An alternative configuration of a drug pump 10 is shown in FIG. 7, with the drug pump 10 further including a power and control system 400. A sterile fluid conduit 30 located at the fluid pathway connection 300 and leading to insertion mechanism 200 is also visible in FIG. 7. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system. In a preferred embodiment, the activation mechanism is a start button 14 that is located through the pump housing 12, such as through an aperture between upper housing 12A and lower housing 12B, and which contacts a control arm 40 of the power and control system. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12 is described in further detail hereinafter with reference to other components and embodiments of the present invention.

Drug pump 10 is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 1C) may be provided in one embodiment as a safety feature to ensure that the power and control system, or the activation mechanism 14, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system to permit activation. In still other embodiments, the on-body sensor can be electrically based such as, for example, a capacitive- or impedance-based sensor which must detect tissue before permitting activation of the power and control system. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Figure 2A:
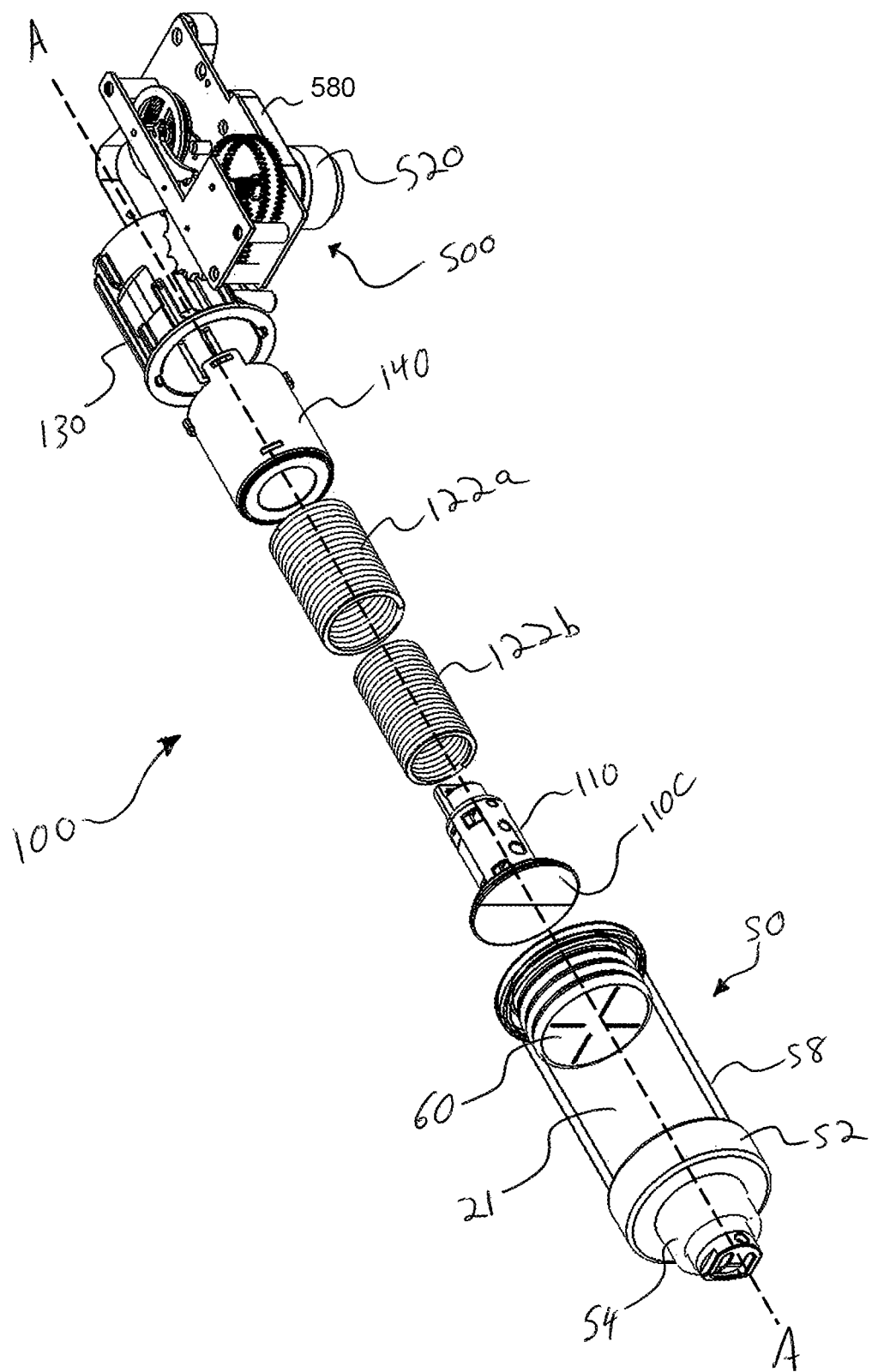
FIG. 2A shows an exploded view, along an axis "A," of a drive mechanism and drug container, of one embodiment of the present invention.

Power and Control System:

As will be described further below, as force to translate a plunger seal 60 is provided by at least one biasing member 122*a*, 122*b* (FIG. 2A), power and control systems are optional in drug delivery pumps of the present invention.

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 100. In one embodiment, the power and control system interfaces with the control arm 40 to identify when the on-body sensor 24 and/or the activation mechanism 14 have been activated. The power and control system may also interface with the status indicator 16 of the pump housing 12, which may be a transmissive or translucent material which permits light transfer, to provide visual feedback to the user. The power and control system interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system is configured to provide a dispensing status signal via the status indicator 16. After the drug has been administered into the body of the user and after the end of any additional dwell time, to ensure that substantially the entire dose has been delivered to the user, the power and control system may provide an okay-to-remove status signal via the status indicator 16. This may be independently verified by the user by viewing the drive mechanism and drug dose delivery through the window 18 of the pump housing 12. Additionally, the power and control system may be configured to provide one or more alert signals via the status indicator 16, such as for example alerts indicative of fault or operation failure situations.

The power and control system may additionally be configured to accept various inputs from the user to dynamically control the drive mechanisms 100 to meet a desired drug delivery rate or profile. For example, the power and control system may receive inputs, such as from partial or full activation, depression, and/or release of the activation mechanism 14, to set, initiate, stop, or otherwise adjust the control of the drive mechanism 100 via the power and control system to meet the desired drug delivery rate or profile. Similarly, the power and control system may be configured to receive such inputs to adjust the drug dose volume; to prime the drive mechanism, fluid pathway connection, and fluid conduit; and/or to start, stop, or pause operation of the drive mechanism 100. Such inputs may be received by the user directly acting on the drug pump 10, such as by use of the activation mechanism 14 or a different control interface, or the system 400 may be configured to receive such inputs from a remote control device. Additionally or alternatively, such inputs may be pre-programmed.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Fluid Pathway Connection:

A number of fluid pathway connections may be utilized within the embodiments of the present invention. Generally, a suitable fluid pathway connection includes a sterile fluid conduit, a piercing member, and a sterile sleeve attached to a drug container or a sliding pierceable seal integrated within a drug container. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In one such embodiment, the fluid pathway connection may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connection may be integrated into a drug container as described in International Patent Application No. PCT/US2013/030478, for example, which is included by reference herein in its entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The sliding pierceable seal is caused to slide towards the cap, causing it to be pierced by the piercing member retained within the integrated sterile fluid pathway connection. Accordingly, the integrated sterile fluid pathway connection is connected (i.e., the fluid pathway is opened) by the combination pneumatic/hydraulic force of the air/gas and drug fluid within the drug chamber created by activation of a drive mechanism. Once the integrated sterile fluid pathway connection is connected or opened, drug fluid is permitted to flow from the drug container, through the integrated sterile fluid pathway connection, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connection utilized by the drug pump, the drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Insertion Mechanism:

A number of insertion mechanisms may be utilized within the drug pumps of the present invention. The pump-type delivery devices of the present invention may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present invention.

In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the body of the user. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit 30 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 254 (shown in FIG. 1C).

According to at least one embodiment of the present invention, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. The lockout pin(s) 208 (FIG. 7) may be directly displaced by user depression of the activation mechanism 14. As the user disengages any safety mechanisms, such as an optional on-body sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows of the insertion mechanism housing. Displacement of the lockout pin(s) 208 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

Figure 2B:
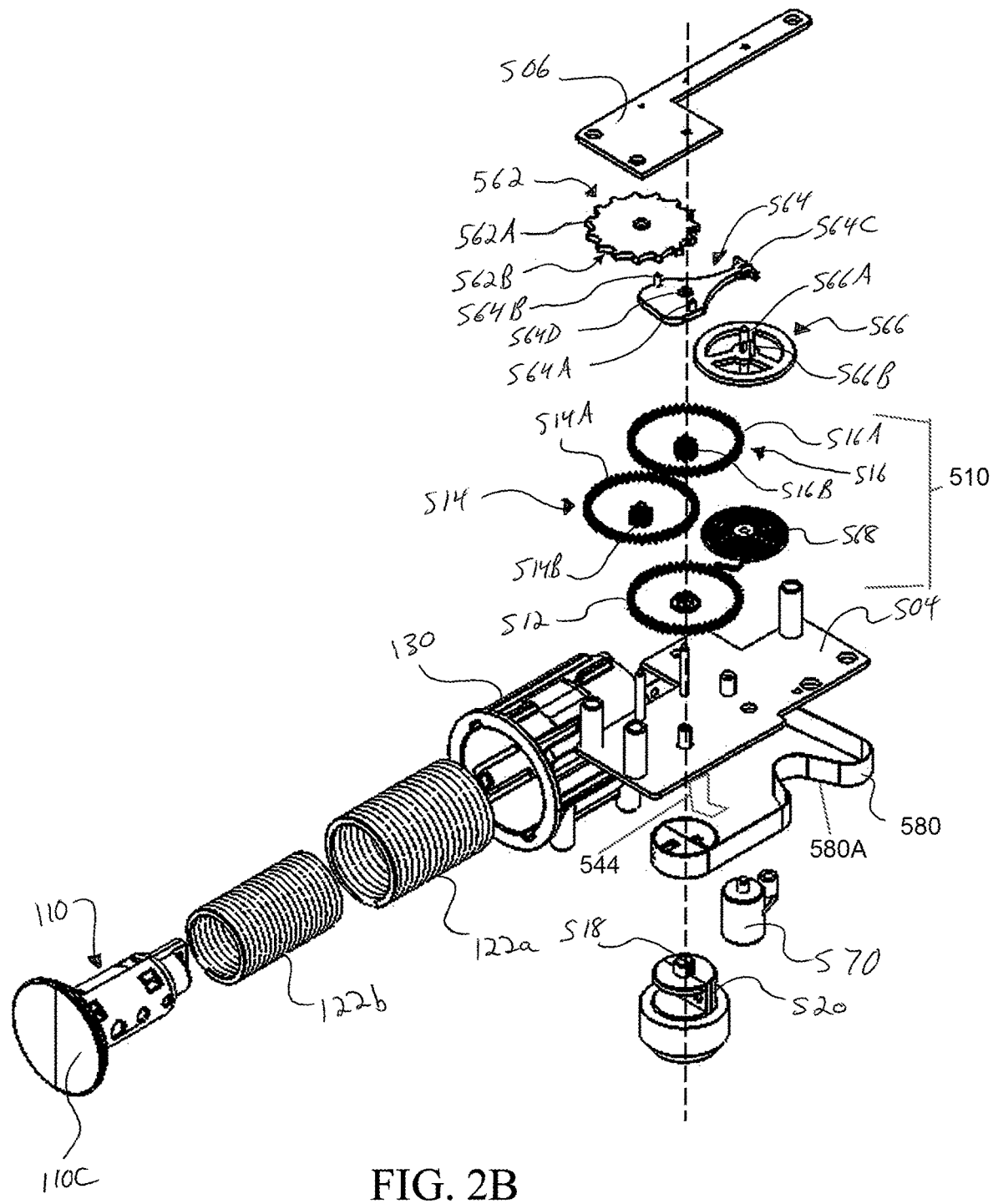
FIG. 2B shows an exploded view, along an axis "B," of one embodiment of the present invention (biasing member, cover sleeve, plunger seal, barrel, and cap are not shown for clarity)
Figure 3A:
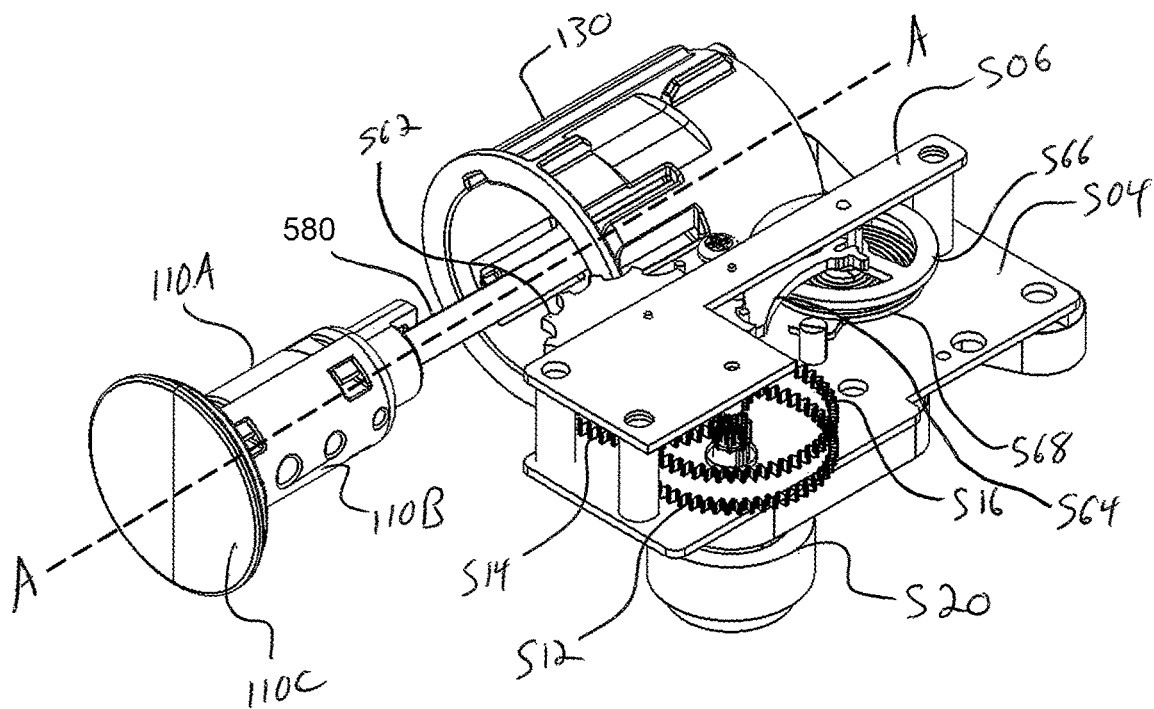
FIG. 3A shows an isometric view of a controlled delivery drive mechanism, according to at least one embodiment of the present invention.

Drive Mechanism:

With reference to the embodiments shown in FIGS. 2 and 3, drive mechanism 100 includes a drive housing 130, and a drug container 50 having a cap 52, a pierceable seal (not visible), a barrel 58, and a plunger seal 60. A drug chamber 21, located within the barrel 58 between the pierceable seal and the plunger seal 60, may contain a drug fluid for delivery through the insertion mechanism and drug pump into the body of the user. The seals described herein may be comprised of a number of materials but are, in a preferred embodiment, comprised of one or more elastomers or rubbers. The drive mechanism may further include a connection mount 54 to guide the insertion of the piercing member of the fluid pathway connection into the barrel 58 of the drug container 50. The drive mechanism 100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connection, for delivery through the fluid pathway connection, sterile fluid conduit, and insertion mechanism into the body of the user.

In one particular embodiment, the drive mechanism 100 employs one or more compression springs as the biasing member(s). Upon activation of the drug pump by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connection may be connected through the pierceable seal prior to, concurrently with, or after activation of the drive mechanism to permit fluid flow from the drug container, through the fluid pathway connection, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail herein.

Referring now to the embodiment of the drive mechanism shown in FIG. 2 and FIG. 3, the drive mechanism 100 includes a drug container 50 having a cap 52, a pierceable seal (not visible), a barrel 58, and a plunger seal 60, and optionally a connection mount 54. The drug container 50 is mounted to a distal end of a drive housing 130. Compressed within the drive housing 130, between the drug container 50 and the proximal end of the housing 130, are drive biasing members 122a and 122b and a piston 110, wherein the drive biasing members 122a, 122b are configured to bear upon an interface surface 110C of the piston 110, as described further herein. Optionally, a cover sleeve 140 may be utilized between the drive biasing members 122 and the interface surface 110C of the piston 110 to, for example, promote more even distribution of force from the drive biasing member 122 to the piston 110, prevent buckling of the drive biasing member 122, and/or hide biasing members 122 from user view. Interface surface 110C of piston 110 is caused to rest substantially adjacent to, or in contact with, a proximal end of seal 60. Although the embodiments shown in FIGS. 2 and 3 show a plurality of biasing members it is also contemplated that a single biasing member may be used.

Figure 3B:
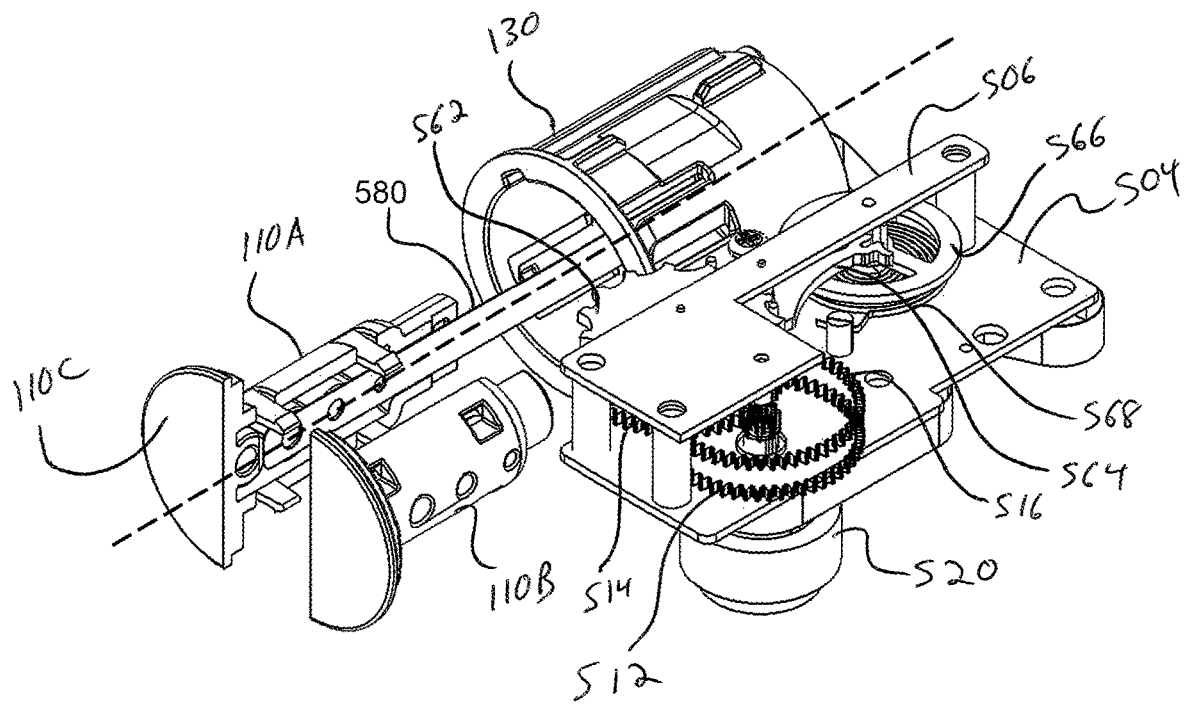
FIG. 3B shows an isometric view of a controlled delivery drive mechanism, according to at least one embodiment of the present invention (the piston is shown exploded to illustrate attachment of tether)

As best shown in FIG. 3B, the piston 110 may be comprised of two components 110A and 110B and have an interface surface 110C to contact the plunger seal. A tether, ribbon, string, or other retention strap (referred to herein as the "tether" 580) may be connected at one end to the piston 110A, 110B. For example, the tether 580 may be connected to the piston 110A, 110B by retention between the two components of the piston 110A, 110B when assembled. The tether 580 is connected at another end to a winch drum 520 of a delivery control mechanism 500. Through the use of the winch drum 520 connected to one end of the tether 580, and the tether 580 connected at another end to the piston 110A, 110B, the regulating mechanism 500 functions to control, meter, provide resistance, or otherwise prevent free axial translation of the piston 110A, 110B and plunger seal 60 utilized to force a drug substance out of a drug container 50. Accordingly, the regulating mechanism 500 and the drive mechanism 100 (collectively referred to herein as the "controlled delivery drive mechanism") together function to control the rate or profile of drug delivery to the user.

As shown in FIGS. 2 and 3, in the embodiments of the present invention, the regulating mechanism 500 is an escapement regulating mechanism. The escapement regulating mechanism retards or restrains the distribution of tether 580, only allowing it to advance at a regulated or desired rate. This restricts movement of piston 110 within barrel 58, hence controlling the movement of plunger seal 60 and delivery of the drug contained in chamber 21. As the plunger seal 60 advances in the drug container 50, the drug substance is dispensed through the sterile pathway connection 300, conduit 30, insertion mechanism 200, and into the body of the user for drug delivery. In turn, tension on tether 580, caused by the force of biasing member 122 on piston 110, imparts a torque on winch drum 520 which is transferred through gear train 510 to the escapement regulating mechanism. Optionally, a power spring may be included, coupled to the escapement regulating mechanism. This may be done in order to impart additional torque to the winding drum and/or gear train.

In at least one embodiment of the present invention, the drive mechanism 100 utilizes an escapement regulating element 500. The regulating element 500 further includes one or more gears 512, 514, 516 of a gear train 510. One or more of the gears 512, 514, 516 may be, for example, compound gears having a small diameter gear attached at a shared center point to a large diameter gear. First gear 512 alternatively referred to as a winch gear, may be rotationally coupled to winch drum 520, for example by a keyed shaft, thereby coupling rotation of gear train 510 to winch drum 520. First gear 512 engages the small diameter gear 514B of compound gear 514 such that rotational movement of the first gear 512 is conveyed by engagement of the gears (such as by engagement of corresponding gear teeth) to the compound gear 514. Large gear 514A of compound gear 514 engages the small gear 516B of a second compound gear 516, conveying rotation thereto. Large gear 516A of second compound gear 516 engages small gear 562B of escape wheel 562, thereby coupling rotation of escape wheel 562 to winch drum 520. Rotation of the gear train 510 may be coupled to winch drum 520 thereby controlling the distribution of tether 580, and the rate of movement of plunger seal 60 within barrel 58 to force a fluid from drug chamber 21. The rotational movement of the winch drum 520, and thus the axial translation of the piston 110 and plunger seal 60, are metered, restrained, or otherwise prevented from free axial translation by other components of the escapement regulating element 500, as described herein.

The escape wheel 562 is a compound gear having escape teeth around the circumference of a large diameter escape gear 562A and a small diameter gear 562B (not visible) configured to engage the gear train 510 and meter, restrain, or otherwise prevent free rotational movement thereof. The escapement regulating element 500 further includes a lever 564. The lever 564 has pins 564A,B and prong 564C. Prong 564C movably engages a post 566A and is configured to removably engage an impulse pin 566B of a balance wheel 566. The balance wheel 566 engages and functions as an oscillator around a pivot point 564D in combination with a hair spring 568. The gear train 510, escape wheel 562, balance wheel 566, hair spring 568, and lever 564 may be mounted on and able to freely rotate or move on a first plate 504 and/or a second plate 506. The first plate 504 and second plate 506 may utilize one or more spacer columns to maintain the desired spacing between components and one or more pivot pins upon which the components may be mounted and freely rotated. An electromechanical actuator 570 may be provided in addition to or in lieu of the hair spring 568. Electromechanical actuator 570 may be configured to control and/or adjust the rotation and/or oscillation of balance wheel 566 as will be discussed further hereinafter.

The function of the escape wheel 562, balance wheel 566, hair spring 568, and lever 564 components of the escapement regulating element 500 are explained with reference to FIG. 2B and FIGS. 4A-4H. The escape wheel 562 and lever 564 may initially be in an activation position, as shown in FIG. 4A. The escape wheel 562 and lever 564 generally function to perform two steps, termed the locking action and the impulse action. These two actions are illustrated in FIG. 4B and FIG. 4C, respectively, and in which the gear train 510 is applying a clockwise torque on the escape wheel 562. The clockwise torque may come as a result of biasing members 122 applying a force to piston 110 which in turn applies a tension to tether 580. The tension of tether 580 imparts a torque on winding drum 520 which is transmitted through gear train 510 to escape wheel 562. Optionally, a power spring may additionally be used to impart torque to gear train 510. In the locking action, one of two lever pins 564A,B blocks escape wheel 562 rotation on the radial face of a tooth on the escape gear 562A. This locks the gear train 510 between impulse actions. In the impulse action, a lever pin 564A,B slides up to this tooth face due to action of the balance wheel 566 on the lever 564. The escape wheel becomes unlocked and does mechanical work on the lever pin 564A, B via a sliding action, which in turn imparts kinetic energy to the balance wheel 566. The lever 564 pivots upon a pivot point 564D until the opposite pin 564A,B engages with an escape wheel tooth on the escape gear 562A, and the locked state is re-entered after a half tooth advance of the escape wheel 562. The transition from locking action to impulse action is triggered by the balance wheel 566, which functions as an oscillator in combination with the hair spring 568 and/or electromechanical actuator 570. It cycles at a natural frequency that serves as the rate control. Alternatively, the rate can be controlled and/or varied by the electromechanical actuator 570. The balance wheel 566 contains an impulse pin 566B which interacts with the lever 564 at prong 564C. For the impulse phase depicted in FIG. 4C, a clockwise moment on the lever 564 exerts a counterclockwise moment on the balance wheel 566, adding to its kinetic energy. The balance wheel 566 rotates until its kinetic energy is absorbed by the hair spring 568 or until it is caused to stop by electromechanical actuator 570. It stops, reverses, and reengages the impulse pin 566B with the lever 564. A complete cycle is shown in the transition between FIGS. 4D-4H. For example, a motor (e.g., a DC motor, AC motor, or stepper motor) or a solenoid (e.g., linear solenoid, rotary solenoid) may be used to rotate the balance wheel. This electromechanical actuator may be used in addition to the hair spring or in place of the hair spring. The electromechanical actuator may be controlled by the power and control system. By providing an electromechanical actuator the rate of drug delivery may be adjusted and/or controlled. In one embodiment, electromechanical actuator 570 is a rotary solenoid. Upon receipt of an input signal from the power and control system the core of the rotary solenoid may rotate. This rotation may be imparted to balancing wheel 566 by, for example, a keyed shaft. The rotary solenoid may later, upon either removal of the input signal or the receipt of a second input signal, rotate the balancing wheel back in the opposite direction or, alternatively, a hair spring may be used to return the balancing wheel in the opposite direction. This action could similarly be performed by a linear solenoid using an appropriate linkage to convert the linear motion of the solenoid core to rotational motion of the balancing wheel. A motor may also be configured to perform similarly.

To unlock the escapement regulating mechanism 500, the balance wheel 566 must have enough kinetic energy to drag the lever pin 564A,B up the face of the tooth of the escape gear 562A of the escape wheel 562. If the impulse action adds less energy than is lost to friction, the balance wheel 566 will rotate less and less and finally stall, locking the escapement regulating mechanism 500. If the escapement stops in this way under load, it will not restart easily. To be self-starting, the hair spring 568 must align the lever 564 along the axis connecting the pivot of the escape wheel 562 and the pivot of the balance wheel 566, as shown in FIG. 4A. The lever pins 564A,B will be positioned so that a bevel tooth face can immediately start an impulse action upon application of a drive torque. This alignment can occur only with the escapement regulating mechanism 500 in an unloaded state. The tension on the tether provided by the force of the biasing member 122 on the piston 110 must be isolated from the escapement regulating mechanism 500 until the start of delivery. This may be done by, for example, providing a lock-out feature which, in a first configuration, prevents motion of piston 110. After transformation to a second configuration, the lock-out feature does not prevent motion of piston 110 and thereafter the tension on tether 580 acts to create a torque on winding drum 520. Alternatively, escapement regulating mechanism 500 may be initiated by a user imparting a force on an activation mechanism and, directly or indirectly through a power and control system, applying a drive torque to start the initial impulse action. Once the escapement regulating mechanism 500 is initiated, it can be effectively utilized to meter, restrain, or otherwise prevent free rotational movement of the gear train 510, winding drum 520 and piston 110, and, thus, plunger seal 60. In a particular embodiment, the escape wheel 562 is a compound gear having escape teeth around the circumference of a large diameter escape gear 562A and a small diameter gear 562B (not visible). The small diameter gear 562B of the escape wheel 562 engages the drive train 510, which engages with winding drum 520 through rotation shaft 518. This novel configuration directly permits the escape wheel 562 to regulate the rotation of the drive train 510 and winding drum 520, which then efficiently regulates the tether 580 and the piston 110.

Notably, the regulating mechanisms 500 of the present invention do not drive the delivery of fluid substances from the drug chamber 21. The delivery of fluid substances from the drug chamber 21 is caused by the expansion of the biasing member 122 from its initial energized state acting upon the piston 110A, 110B and plunger seal 60. The regulating mechanisms 500 instead function to provide resistance to the free motion of the piston 110A, 110B and plunger seal 60 as they are pushed by the expansion of the biasing member 122 from its initial energized state. The regulating mechanism 500 does not drive the delivery but only controls the delivery motion. The tether limits or otherwise restrains the motion of the piston 110 and plunger seal 60, but does not apply the force for the delivery. According to a preferred embodiment, the controlled delivery drive mechanisms and drug pumps of the present invention include an escapement regulating mechanism indirectly or directly connected to a tether metering the axial translation of the piston 110A, 110B and plunger seal 60, which are being driven to axially translate by the biasing member 122. The rate of drug delivery as controlled by the regulating mechanism may be determined by: selection of the gear ratio of gear train 510; selection of the spring rate of hair spring 568; selection of the diameter of winding drum 520; using electromechanical actuator 570 to control the rate of oscillation and/or rotation of balance wheel 566; or any other method known to one skilled in the art. By using electromechanical actuator 570 to control the oscillation and/or rotation of balance wheel 566 it may be possible to configure a drug pump to provide a variable dose rate (i.e., the rate of drug delivery is varied during a treatment).

In another embodiment, the power and control system of the drug pump is configured to receive one or more inputs to meter the release of the tether 580 by the winch drum 520 and thereby permit axial translation of the piston 110 by the biasing member 122 to translate a plunger seal 60 within a barrel 58. The one or more inputs may be provided by the actuation of the activation mechanism 14, a control interface, and/or a remote control mechanism. The power and control system may be configured to receive one or more inputs to adjust the restraint provided by the tether 580 and winch drum 520 on the free axial translation of the piston 110 upon which the biasing member 122 bears upon to meet a desired drug delivery rate or profile, to change the dose volume for delivery to the user, and/or to otherwise start, stop, or pause operation of the drive mechanism.

The components of the drive mechanism 100, upon activation, may be used to drive axial translation in the distal direction of the plunger seal 60 of the drug container 50. Optionally, the drive mechanism 100 may include one or more compliance features which enable additional axial translation of the plunger seal 60 to, for example, ensure that substantially the entire drug dose has been delivered to the user. For example, the plunger seal 60, itself, may have some compressibility permitting a compliance push of drug fluid from the drug container.

The novel controlled delivery drive mechanisms of the present invention may optionally integrate status indication into the drug dose delivery. By use of one or more status triggers 580A and a corresponding status reader 544, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. As the end-of-dose indication is tied to the piston reaching the end of its axial translation, the drive mechanism and drug pump provide a true end-of-dose indication to the user.

The tether 580 may have one or more status triggers, such as electrical contacts, optical markings, or electromechanical pins or recesses, which are capable of contacting or being recognized by a status reader. In at least one embodiment, an end-of-dose status indication may be provided to the user once the status reader contacts or recognizes the final status trigger positioned on the tether 580 that would contact the status reader at the end of axial travel of the piston 110A, 110B and plunger 60 within the barrel 58 of the drug container 50. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 580 to be read or recognized at positions which correspond with the beginning and end of drug delivery, as well as at desired increments during drug delivery. As the drug pump is activated and drug delivery is begun by release of the biasing member 122 and the resulting force applied to the piston 110A, 110B and plunger seal 60, the rate or profile of drug delivery to the user is controlled by the escapement regulating mechanism, gear assembly, and winch drum 520 releasing the tether 580 and permitting expansion of the biasing member 122 and axial translation of the piston 110A, 110B and plunger seal 60. As this occurs, the status triggers of the tether 580 are contacted or recognized by the status reader and the status of the drive mechanism before, during, and after operation can be relayed to the power and control system to provide feedback to the user. Depending on the number of status triggers located on the tether 580, the frequency of the incremental status indication may be varied as desired. As described above, a range of status readers may be utilized depending on the status triggers utilized by the system.

In a preferred embodiment, the status reader may apply a tensioning force to the tether 580. When the system reaches end-of-dose, the tether 580 goes slack and the status reader 544 is permitted to rotate about a fulcrum. This rotation may operate an electrical or electromechanical switch, for example a switch, signaling slack in the tether 580 to the power and control system. Additionally, a gear of gear train 510 may act as an encoder along with a sensor. The sensor/encoder combination is used to provide feedback of gear train rotation, which in turn can be calibrated to the position of piston 110 when there is no slack in the tether 580. Together, the status reader and sensor/encoder may provide positional feedback, end-of-dose signal, and error indication, such as an occlusion, by observing slack in the tether 580 prior to reaching the expected number of motor rotations as counted by the sensor/encoder.

Figure 5A:
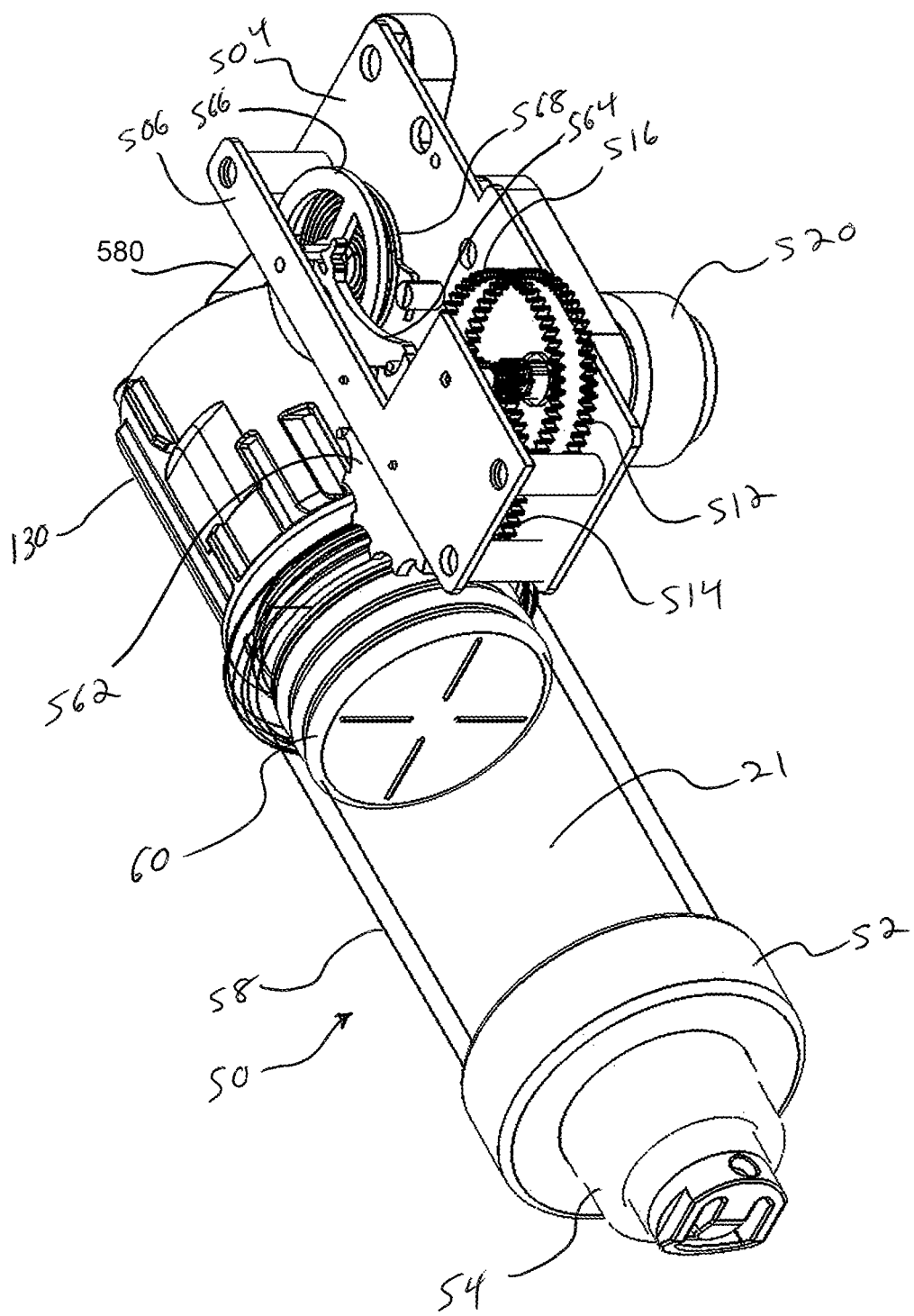
FIG. 5A shows an isometric view of the drive mechanism and drug container shown in FIG. 2 in an initial inactive state.
Figure 5B:
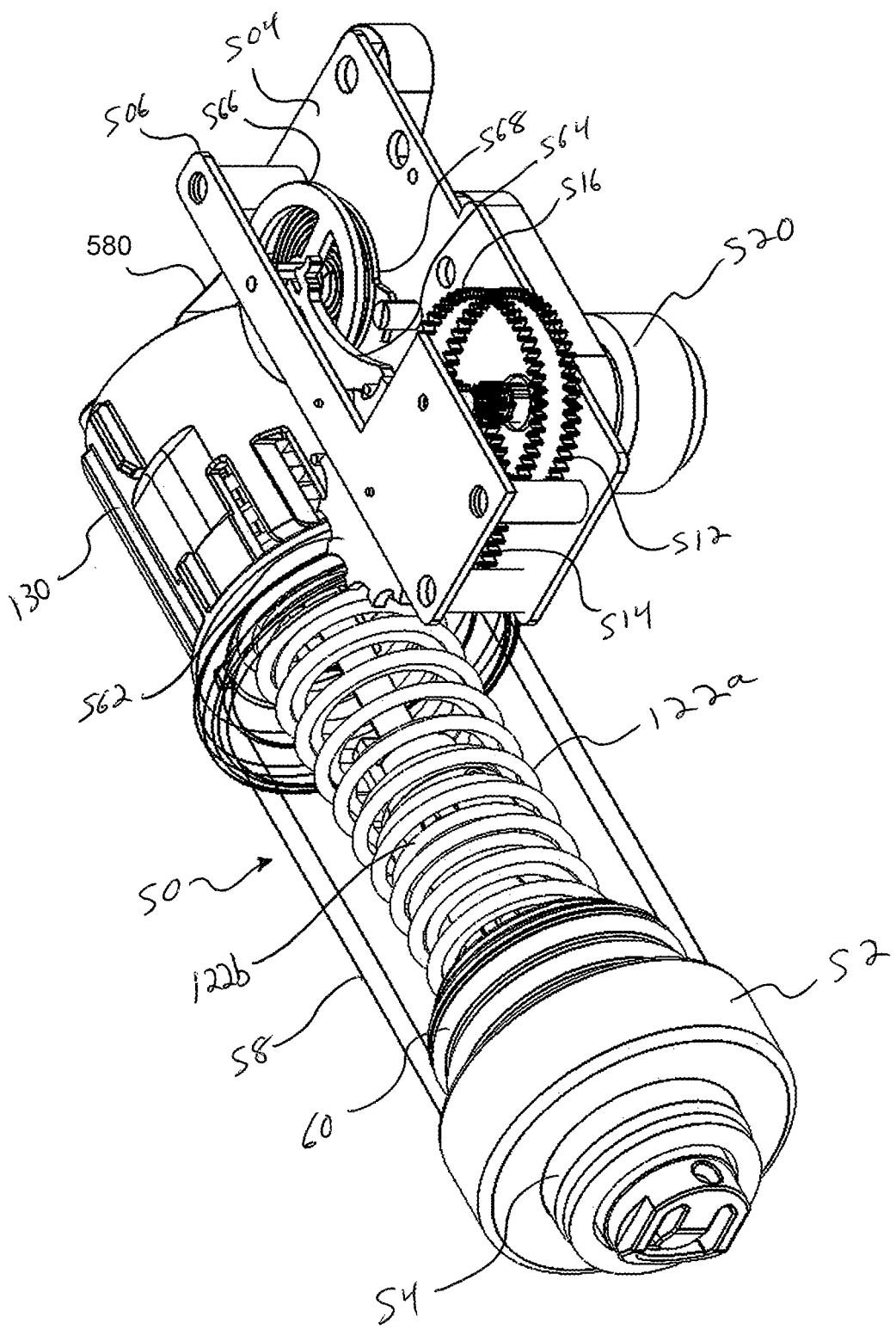
FIG. 5B shows an isometric view of the drive mechanism shown in FIG. 2 as the mechanism completes drug delivery.
Figure 6A:
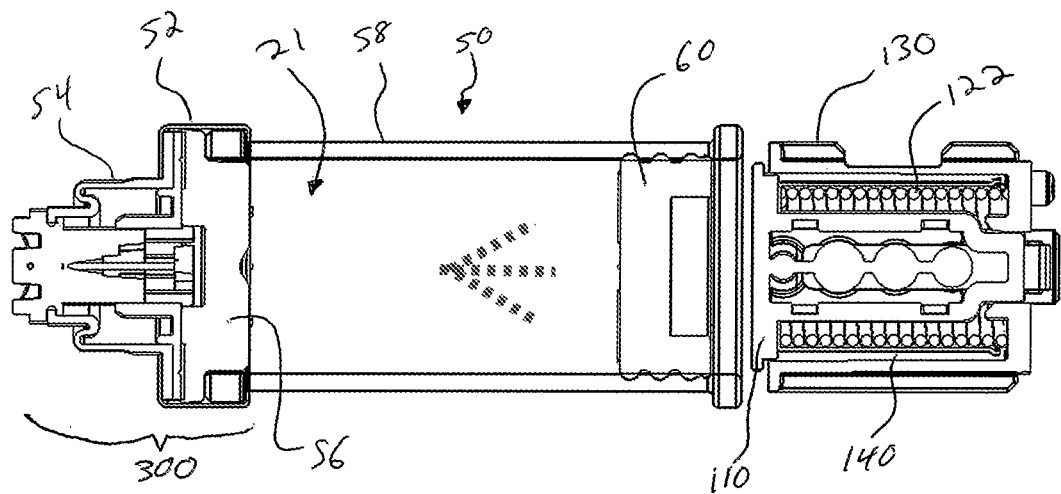
FIG. 6A shows a cross-sectional view of the drive mechanism shown in FIG. 2 in an initial inactive state.

Further aspects of the novel drive mechanism will be described with reference to FIGS. 5A-5B and 6A-6C. FIG. 5A shows an isometric view of the drive mechanism, according to at least a first embodiment, during its initial locked stage. A fluid, such as a drug fluid, may be contained within barrel 58, in a drug chamber 21 between plunger seal 60 and a pierceable seal (not visible), for delivery to a user. The pierceable seal is adjacent or retained at least partially within cap 52. Upon activation by the user, a fluid pathway connection may be connected to the drug container through the pierceable seal 56. As described above, this fluid connection may be facilitated by a piercing member of the fluid pathway connection which pierces the pierceable seal and completes the fluid pathway from the drug container, through the fluid pathway connection, the fluid conduit, the insertion mechanism, and the cannula for delivery of the drug fluid to the body of the user. Initially, one or more locking mechanisms (not shown) may retain the biasing member 122 in an initial energized position within piston 110A, 110B. Directly or indirectly upon activation of the device by the user, the locking mechanism may be removed to permit operation of the drive mechanism. Removal of the locking mechanism may permit the biasing member to impart a force to piston 110 and therefore to tether 580. This force on tether 580 imparts a torque on winding drum 520 which causes the gear train and escapement regulating mechanism to begin motion. As shown in FIG. 6A, the piston 110 and biasing member 122 are both initially in a compressed, energized state behind the plunger seal 60. The biasing member 122 may be maintained in this state until activation of the device between internal features of drive housing 130 and interface surface 110C of piston 110A, 110B. As the locking mechanism is removed or displaced, biasing member 122 is permitted to expand (i.e., decompress) axially in the distal direction (i.e., in the direction of the hatched arrow). Such expansion causes the biasing member 122 to act upon and distally translate interface surface 110C and piston 110, thereby distally translating plunger seal 60 to push drug fluid out of the drug chamber 21 of barrel 58.

Figure 6B:
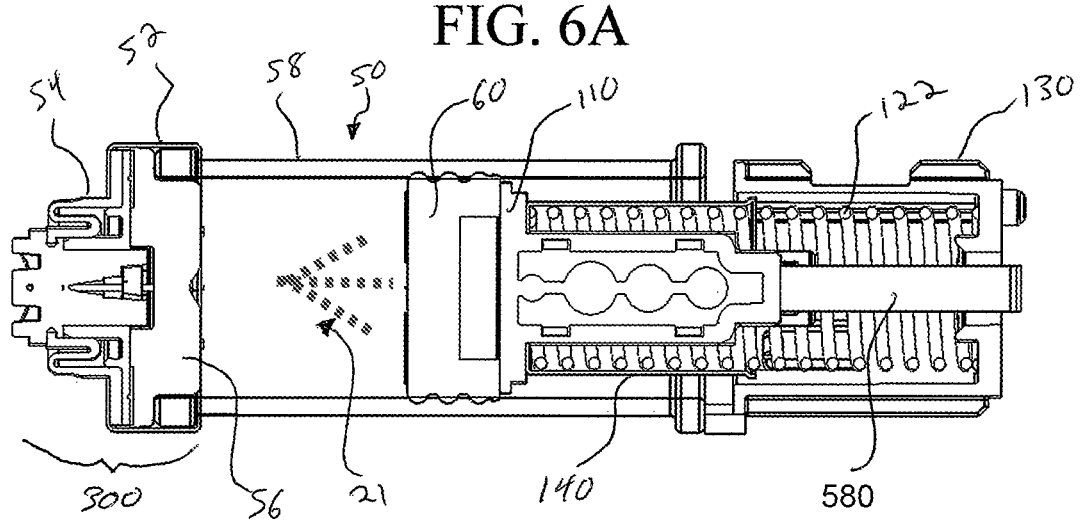
FIG. 6B shows a cross-sectional view of the drive mechanism shown in FIG. 2 in an actuated state as the mechanism controls the rate or profile of drug delivery.

As shown in FIG. 6B, such distal translation of the piston 110A, 110B and plunger seal 60 continues to force fluid flow out from barrel 58 through the pierceable seal 56. In at least one embodiment, an end-of-dose status indication may be provided to the user once the status reader contacts or recognizes a status trigger positioned on the tether 580 to substantially correspond with the end of axial travel of the piston 110A, 110B and plunger seal 60 within the barrel 58 of the drug container 50. The status triggers are positioned along the tether 580 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 580 to be read or recognized at positions which correspond with the beginning and end of drug delivery, as well as at desired increments during drug delivery. As shown, tether 580 passes substantially axially through the drive mechanism housing 130, the biasing member 122, and connects to the piston 110A, 110B to restrict the axial translation of the piston 110A, 110B and the plunger seal 60 that resides adjacent thereto.

The novel embodiments of the present invention may be utilized to meter, restrain, or otherwise prevent free rotational movement of winding drum 520 and, thus, axial translation of the components of the controlled delivery drive mechanism 100. Accordingly, the escapement regulating mechanism 500 only controls the motion of the drive mechanism, but does not apply the force for the drug delivery. One or more additional biasing members 122, such as compression springs, may be utilized to drive or assist the driving of the piston 110. For example, a compression spring may be utilized within the drive housing 130 for this purpose. The escapement regulating mechanism 500 only controls, meters, or regulates such action. A mechanical timing system, such as the escapement regulating mechanism described herein, may be utilized to allow the piston 110 and plunger seal 60 to translate axially a controlled distance, or a controlled volume, and may be utilized to meet a desired delivery rate or profile. The timing system can be controlled by quartz timing instead of mechanical timing, as would be appreciated by one having ordinary skill in the art. For quartz timing, a battery provides power to a microchip and circuit. The quartz crystal oscillates at a precise frequency. Alternate electrical timing mechanisms such as, for example, RC timing mechanisms, may also be used, including clock functions commonly found in microprocessors. Depending on the period that the delivery is planned to occur over, the microchip drives a motor based on a number of quartz crystal oscillations or other timing signals. The motor releases motion of a drive train to control the axial translation of a plunger in a similar manner as described herein for the mechanical timing system.

Figure 6C:
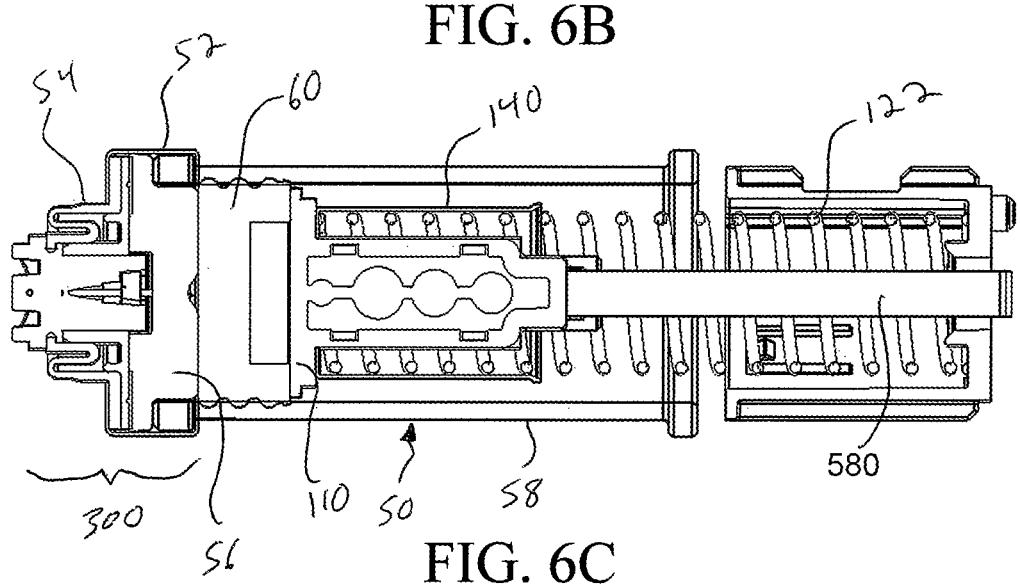
FIG. 6C shows a cross-sectional view of the drive mechanism shown in FIG. 2 as the mechanism completes drug delivery and, optionally, performs a compliance push to ensure completion of drug delivery.

The delivery control mechanisms 500 of the present invention do not drive the delivery of fluid substances from the drug chamber 21. The delivery of fluid substances from the drug chamber 21 is caused by the expansion of the biasing member 122 from its initial energized state acting upon the piston 110A, 110B and plunger seal 60. The delivery control mechanisms 500 instead function to provide resistance to the free motion of the piston 110A, 110B and plunger seal 60 as they are pushed by the expansion of the biasing member 122 from its initial energized state. As the delivery control mechanisms 500 release the tether 580, the biasing member 122 is permitted to continue its expansion from its energized state and drive the piston 110A, 110B and plunger seal 60 until the plunger seal 60 has substantially contacted the pierceable seal 56. This is visible in the cross-sectional view provided in FIG. 6C. At this point, substantially all of the drug substance has been pushed out of the drug chamber 21 through the fluid pathway connection 300 for drug delivery to the user. A status trigger may be configured along the tether 580 to correspond with this position of the piston 110A, 110B, such that, as the piston 110A, 110B reaches its end of axial travel, a status trigger is read or recognized by the status reader to provide true end-of-dose indication to the user. As stated above, the status triggers may be positioned along the tether 580 to be read or recognized at positions which correspond with the beginning and end of drug delivery, as well as at desired increments during drug delivery. The controlled delivery drive mechanisms and/or drug pumps of the present invention may additionally enable a compliance push to ensure that substantially all of the drug substance has been pushed out of the drug chamber 21. The plunger seal 60, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container, as shown in FIG. 6C. Additionally or alternatively, an electromechanical status switch and interconnect assembly may be utilized to contact, connect, or otherwise enable a transmission to the power and control system to signal end-of-dose to the user. For example, the status switch may be located distal to the pierceable seal 56 and the interconnect located proximal to the plunger seal 60 such that, upon substantially complete axial translation (and optional compliance push) of the plunger seal 60 within the barrel 58, the status switch and interconnect coordinate to enable a transmission to the power and control system to signal end-of-dose to the user. This configuration further enables true end-of-dose indication to the user.

In at least one embodiment, incremental status indication may be provided to the user by reading or recognizing the rotational movement of one or more gears of gear train 510. As the gear train 510 rotates, a status reader may read or recognize one or more corresponding status triggers on one of the gears in the gear train to provide incremental status indication before, during, and after operation of the variable rate controlled delivery drive mechanism. A number of status readers may be utilized within the embodiments of the present invention. For example, the drive mechanism may utilize a mechanical status reader which is physically contacted by gear teeth of one of the gears of the gear train. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the user. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear train (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present invention to provide incremental status indication to the user. While the drive mechanisms of the present invention are described with reference to the gear train and escapement regulating mechanism shown in the figures, a range of configurations may be acceptable and capable of being employed within the embodiments of the present invention, as would readily be appreciated by an ordinarily skilled artisan. Accordingly, the embodiments of the present invention are not limited to the specific gear train and escapement regulating mechanism described herein, which is provided as an exemplary embodiment of such mechanisms for employment within the controlled delivery drive mechanisms and drug delivery pumps.

Assembly and/or manufacturing of controlled delivery drive mechanism 100, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 50 may first be assembled and filled with a fluid for delivery to the user. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 may guide the insertion of the piercing member of the fluid pathway connection into the barrel 58 of the drug container 50. The drug container 50 may then be mounted to a distal end of drive housing 130.

One or more drive biasing members 122 may be inserted into a distal end of the drive housing 130. Optionally, a cover sleeve 140 may be inserted into a distal end of the drive housing 130 to substantially cover biasing member 122. A piston may be inserted into the distal end of the drive housing 130 such that it resides at least partially within an axial pass-through of the biasing member 122 and the biasing member 122 is permitted to contact a piston interface surface 110C of piston 110A, 110B at the distal end of the biasing member 122. An optional cover sleeve 140 may be utilized to enclose the biasing member 122 and contact the piston interface surface 110C of piston 110A, 110B. The piston 110A, 110B and drive biasing member 122, and optional cover sleeve 140, may be compressed into drive housing 130. Such assembly positions the drive biasing member 122 in an initial compressed, energized state and preferably places a piston interface surface 110C in contact with the proximal surface of the plunger seal 60 within the proximal end of barrel 58. The piston, piston biasing member, contact sleeve, and optional components, may be compressed and locked into the ready-to-actuate state within the drive housing 130 prior to attachment or mounting of the drug container 50. The tether 580 is pre-connected to the proximal end of the piston 110A, 110B and passed through the axial aperture of the biasing member 122 and drive mechanism 130, and then wound through the interior of the drug pump with the other end of the tether 580 wrapped around the winch drum 520 of the regulating mechanism 500.

A fluid pathway connection, and specifically a sterile sleeve of the fluid pathway connection, may be connected to the cap and/or pierceable seal of the drug container. A fluid conduit may be connected to the other end of the fluid pathway connection which itself is connected to the insertion mechanism such that the fluid pathway, when opened, connected, or otherwise enabled travels directly from the drug container, fluid pathway connection, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug pump, as shown in FIG. 1B.

Certain optional standard components or variations of drive mechanism 100 or drug pump 10 are contemplated while remaining within the breadth and scope of the present invention. For example, the embodiments may include one or more batteries utilized to power a motor or solenoid, drive mechanisms, and drug pumps of the present invention. A range of batteries known in the art may be utilized for this purpose. Additionally, upper or lower housings may optionally contain one or more transparent or translucent windows 18, as shown in FIG. 1A, to enable the user to view the operation of the drug pump 10 or verify that drug dose has completed. Similarly, the drug pump 10 may contain an adhesive patch 26 and a patch liner 28 on the bottom surface of the housing 12. The adhesive patch 26 may be utilized to adhere the drug pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug pump 10 in contact with the body of the user. Removal of the patch liner 28 may further remove the sealing membrane 254 of the insertion mechanism 200, opening the insertion mechanism to the body of the user for drug delivery (as shown in FIG. 1C).

Similarly, one or more of the components of controlled delivery drive mechanism 100 and drug pump 10 may be modified while remaining functionally within the breadth and scope of the present invention. For example, as described above, while the housing of drug pump 10 is shown as two separate components upper housing 12A and lower housing 12B, these components may be a single unified component. As discussed above, a glue, adhesive, or other known materials or methods may be utilized to affix one or more components of the controlled delivery drive mechanism and/or drug pump to each other. Alternatively, one or more components of the controlled delivery drive mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the controlled delivery drive mechanisms and drug pumps disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present invention control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present invention may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. The novel controlled delivery drive mechanisms of the present invention may be directly or indirectly activated by the user. Furthermore, the novel configurations of the controlled delivery drive mechanism and drug pumps of the present invention maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly.

Manufacturing of a drug pump includes the step of attaching both the controlled delivery drive mechanism and drug container, either separately or as a combined component, to an assembly platform or housing of the drug pump. The method of manufacturing further includes attachment of the fluid pathway connection, drug container, and insertion mechanism to the assembly platform or housing. The additional components of the drug pump, as described above, including the power and control system, the activation mechanism, and the control arm may be attached, pre-formed, or pre-assembled to the assembly platform or housing. An adhesive patch and patch liner may be attached to the housing surface of the drug pump that contacts the user during operation of the device.

A method of operating the drug pump includes the steps of: activating, by a user, the activation mechanism; displacing a control arm to actuate an insertion mechanism; and actuating a power and control system to activate a controlled delivery drive mechanism to drive fluid drug flow through the drug pump according to a controlled rate or drug delivery profile. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the controlled delivery drive mechanism by the expansion of the biasing member acting upon a piston within a drug container to force fluid drug flow through the drug container, the fluid pathway connection, a sterile fluid conduit, and the insertion mechanism for delivery of the fluid drug to the body of a user, wherein a regulating mechanism acting to restrain the distribution of a tether is utilized to meter the free axial translation of the piston. The method of operation of the insertion mechanism and the drug pump may be better appreciated with reference to FIGS. 5A-5B and FIGS. 6A-6C, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A controlled delivery drive mechanism for a drug delivery pump, comprising:
    a drive housing;
    a piston having an interface surface;
    at least one biasing member initially retained in an energized state and configured to bear upon the interface surface of the piston;
    a tether connected at one end to the piston and at another end to a winch drum, the tether configured to restrain expansion of the at least one biasing member; and
    an escapement regulating mechanism configured to meter release of the tether by the winch drum, wherein release of the at least one biasing member from the initial energized state applies tension to the tether, the tension to the tether imparting a drive torque to the escapement regulating mechanism and initiating an impulse action of the escapement regulating mechanism to initiate the metered release of the tether, the metered release of the tether providing for controlled expansion of the at least one biasing member.

2. The controlled delivery drive mechanism of claim 1, further comprising:
    a drug container having a plunger seal located within a barrel, wherein the piston is configured to axially translate the plunger seal within the barrel.

3. The controlled delivery drive mechanism of claim 2, wherein the drug container contains a drug fluid within a drug chamber of the barrel.

4. The controlled delivery drive mechanism of claim 1, wherein the metering of the tether by the escapement regulating mechanism controls a rate or profile of drug delivery to a user.

5. The controlled delivery drive mechanism of claim 1, wherein the escapement regulating mechanism comprises a gear train having one or more gears, wherein rotation of at least one gear of the gear train is coupled to rotation of the winch drum.

6. The controlled delivery drive mechanism of claim 5, wherein the escapement regulating mechanism further comprises a lever and an escape wheel configured to engage with the gear train and meter rotational movement of the gear train.

7. The controlled delivery drive mechanism of claim 6, wherein the escape wheel is a compound gear including at least two escape gears of different diameter, one of the at least two escape gears comprising escape teeth and another of the at least two escape gears configured to engage with the gear train.

8. The controlled delivery drive mechanism of claim 6, wherein the lever includes pins and a prong, the prong configured to moveably engage a post and an impulse pin of a balance wheel, the balance wheel configured to oscillate about the post in combination with a hair spring.

9. The controlled delivery drive mechanism of claim 8 further comprising an actuator that at least partially controls oscillation of the balance wheel.

10. The controlled delivery drive mechanism of claim 9, wherein the actuator is a mechanical actuator, an electrical actuator, or an electromechanical actuator.

11. The controlled delivery drive mechanism of claim 6, wherein the gear train comprises a winch gear rotationally coupled to the winch drum and configured to engage at least one compound gear, the at least one compound gear configured to engage directly or indirectly with the escape wheel, the at least one compound gear thereby coupling rotation of the escape wheel to rotation of the winch drum.

12. The controlled delivery drive mechanism of claim 1, further comprising a status reader configured to recognize one or more status triggers incrementally spaced on the tether.

13. The controlled delivery drive mechanism of claim 12, wherein the status reader is an optical status reader and the one or more status triggers are optical status triggers.

14. The controlled delivery drive mechanism of claim 12, wherein the status reader is an electromechanical status reader and the one or more status triggers are electromechanical status triggers.

15. The controlled delivery drive mechanism of claim 1, wherein the escapement regulating mechanism is configured to transition between the impulse action and a locking action based on oscillating movement of a balance wheel.

16. The controlled delivery drive mechanism of claim 15, wherein a rate of oscillation of the balance wheel provides for a rate of metered release of the tether.

17. A drug delivery pump comprising:
a housing;
an insertion mechanism;
a fluid pathway connection;
a power and control system; and
a controlled delivery drive mechanism comprising:
 a drive housing;
 a piston having an interface surface;
 at least one biasing member initially retained in an energized state and configured to bear upon the interface surface of piston;
 a tether connected at one end to the piston and at another end to a winch drum, the tether configured to restrain expansion of the at least one biasing member; and
 an escapement regulating mechanism configured to meter release of the tether by the winch drum, wherein release of the at least one biasing member from the initial energized state applies tension to the tether, the tension to the tether imparting a drive torque to the escapement regulating mechanism and initiating an impulse action of the escapement regulating mechanism to initiate the metered release of the tether, the metered release of the tether providing for controlled expansion of the at least one biasing member;
wherein the power and control system is configured to receive one or more inputs to meter the release of tether by the winch drum and permit axial translation of the piston by the biasing member.

18. The drug delivery pump of claim 17, wherein the one or more inputs are received from an activation mechanism configured to be acted upon by a user.

19. The drug delivery pump of claim 17, wherein the power and control system is configured to adjust an amount of restraint provided by the tether and winch drum on the axial translation of the piston to start, stop, or pause operation of the drive mechanism based on the one or more inputs.

20. The drug delivery pump of claim 17, wherein the power and control system is configured to adjust an amount of restraint provided by the tether and winch drum on the axial translation of the piston to change a dose volume or a delivery rate for delivery to a user based on the one or more inputs.

* * * * *